(12) United States Patent
Weber et al.

(10) Patent No.: US 6,289,240 B1
(45) Date of Patent: Sep. 11, 2001

(54) FLUID BIOFEEDBACK DEVICE

(75) Inventors: Paul J. Weber, Ft. Lauderdale; Michael R. Weber, Clearwater, both of FL (US); Luiz B. Da Silva, Pleasanton, CA (US); Christopher P. Weber, Ft. Lauderdale, FL (US)

(73) Assignee: Pearl Technology Holdings, LLC., Clearwater, FL (US)

( * ) Notice: Subject to any disclaimer, the term of this patent is extended or adjusted under 35 U.S.C. 154(b) by 0 days.

(21) Appl. No.: 09/352,733

(22) Filed: Jul. 13, 1999

(51) Int. Cl.$^7$ .................................................. A61B 5/04
(52) U.S. Cl. ............................................................. 600/545
(58) Field of Search .................................. 600/545, 306, 600/552, 553, 554, 555, 556, 557, 405, 588, 457; 128/905

(56) References Cited

U.S. PATENT DOCUMENTS

| | | | |
|---|---|---|---|
| 4,110,918 | * 9/1978 | James et al. ........................ | 129/905 |
| 4,801,921 | * 1/1989 | Zigenfus ........................... | 340/573.1 |
| 4,846,157 | * 7/1989 | Sears .................................. | 601/71 |
| 5,546,941 | * 8/1996 | Zeimer et al. ..................... | 600/405 |
| 5,634,463 | * 6/1997 | Hayafuji ............................ | 600/405 |
| 5,808,540 | * 9/1998 | Wheeler et al. .................... | 338/114 |

* cited by examiner

*Primary Examiner*—Eric F. Winakur
*Assistant Examiner*—Brian Szmal
(74) *Attorney, Agent, or Firm*—John P. Wooldridge (57) ABSTRACT

Positive or negative biofeedback is provided by an apparatus using jets of fluid, such as a compressed gas, directed at a targeted area of a body to produce a positive or negative tactile sensation. A stimulus unit is connected to a fluid supply and is positioned on the body, such as the abdomen or back. A sensor unit connected to the stimulus unit is activated, such as by relaxed muscle position or other behavior, which then activates the stimulus unit to open release valves and deliver bursts of small jets of gas to the body. The sensor unit may be remote from the stimulus unit, whereby signals are sent remotely through a control unit to the stimulus unit to activate the release valves.

29 Claims, 8 Drawing Sheets

FLUID BIOFEEDBACK DEVICE

BACKGROUND OF THE INVENTION

1. Field of the Invention

The present invention relates to a biofeedback device using jets of fluid, such as a compressed gas, to stimulate a targeted area on a body and alert the user to modify body position or behavior. More particularly, the device can be used to stimulate abdominal and back muscle control to improve posture and muscle strength, or for behavior modification such as incontinence.

2. Description of Related Art

Biofeedback devices have been developed to serve as aids to persons trying to achieve control over postural or autonomic (self-controlled) body functions. For example, devices have been developed to monitor electrical signals or electrical resistance in the organs (e.g., skin) of the human anatomy, and then send a signal to the individual to indicate the presence of a given body condition or behavior. The signals sent to the individual typically take the form of audible, visual, vibrational, or electrical signals. With practice, the signal imparted to the user can be used by the subject to control or modify the body conditions or behaviors that gave rise to the change in electrical signal or resistance. Autonomic conditions can be monitored and controlled through biofeedback instrumentation and training, including body temperature (thermal), brainwave activity (EEG), and muscle neuron activity (EMG). An example of a modular biofeedback training system is disclosed in U.S. Pat. No. 4,110,918 to James et al.

Biofeedback devices have been developed particularly to strengthen abdominal muscles to provide an improved appearance to the stomach area and to support the back. These devices include weight belts and other abdominal excursion restrictive devices. Restrictive belts merely hold back the abdomen, however, and do not strengthen the musculature. In fact, this type of device may allow the anterior and lateral abdominal musculature to attenuate.

Other devices use audible, electrical, visual, or vibrational signals to remind the wearer to improve posture and abdominal strength. U.S. Pat. No. 4,801,921 to Zigenfus discloses an apparatus where a constant signal, either an electrical charge or vibrational impulse, is applied to the abdominal wall to remind the wearer to contract the abdominal muscles. U.S. Pat. No. 5,808,540 to Wheeler et al. discloses a position sensing and signaling system using audible or vibrational signals to cause the wearer to contract abdominal muscles. U.S. Pat. No. 4,846,157 to Sears discloses an abdomen-circumscribing belt with a battery-operated vibrator that is activated when the wearer's abdomen reaches a predetermined girth.

The present invention provides a variation to these prior art devices by providing a biofeedback signal in the form of tactile stimulation to an animal or human body using small jets of fluid, such as a compressed gas. This tactile stimulation can be a pleasant sensation (for positive feedback), or it can produce a jarring, uncomfortable stimulus that is necessary to elicit a change in the body position or behavior of the subject. This form of biofeedback signal can be incorporated into a device that is relatively inconspicuous to wear, simple in construction, easy to use, and cost-effective to manufacture. The jets of fluid can be activated by a sensor that causes the opening of release valves for the jets either mechanically or electrically.

SUMMARY OF THE INVENTION

The object of the present invention is to provide a biofeedback device using small jets or streams of fluid, such as a compressed gas, as tactile stimuli to a selected region of a subject's body. Upon sensing the gas jets, the subject modifies body position or behavior. The gas jets may produce a positive sensation, providing positive feedback, or may act as an irritant and provide feedback for negative behavior.

The device comprises a stimulus unit, which contains an array or grid of the jets or nozzles for directing a sudden flow of high velocity gas to the skin of the target area. The stimulus unit is connected to a fluid supply, such as a cylinder of compressed gas (e.g., air or $CO_2$), through a fluid release valve. The stimulus unit is capable of being worn next to the body, like a belt, and may include means for maintaining contact with the body. The stimulus unit may be connected directly to a sensor unit, which senses a change in body position or other behavior and activates the release valve to release a burst of jets of gas. This activation can be accomplished through mechanical means, which requires no power source, or the stimulus unit can be activated by an electrical signal powered by a power source (e.g., a battery).

In an alternative embodiment, a control unit may be connected to the sensor unit and the release valve, whereby the sensor unit causes a change in the control unit. The control unit then sends a signal to the release valve to activate the burst of gas jets so as to stimulate the superficial skin and its attendant nerves and cause tactile pleasure or discomfort. Alternatively, the stimulus unit can be connected to a control unit without a sensor unit, where the control unit is programmed to activate the stimulation on a pre-set time schedule or computer-generated randomized pattern, as a reminder or positive stimulus to the subject.

A sensor unit comprises a sensor that may be incorporated into or mechanically connected to an electronic circuit element (e.g., capacitor, inductor, resistor) in the control unit to cause a change in the electrical characteristics of the circuit in a measurable way in response to changes in the sensor. For example, changes induced in the value of a capacitor or inductor alter the resonant frequency of an L-C resonator circuit. Changes in the electrical characteristics of the circuit in the control unit can be detected remotely by the stimulus unit using an electronic interrogation device. The control unit can powered by the interrogator device in the stimulus unit, or the control unit circuit element may be designed for passive interrogation.

The present invention can be used to provide biofeedback stimulus for a wide range of behaviors. For example, the device can be readily designed for strengthening abdominal and back muscles and improving posture by using a pressure sensor unit sensitive to the expansion and contraction of a subject's abdominal or back muscles. As an abdominal muscle training aid, the device is relatively compact and may be worn in a concealed, inconspicuous manner. The stimulus unit may be personally fitted to the wearer, and the sensor unit adjusted specifically for a pre-determined set of limits relative to the pressure between the abdominal wall and the sensor.

The sensor unit can be designed to be remote from the stimulus unit; that is, the stimulus is applied in one area of the body while the sensor unit detects body position or another behavior at another area of the body. The sensor unit can be designed as a chemical sensor to detect an analyte such as urine, for example, for a device to control incontinence. A sensor for detecting compounds in cigarette smoke can be used for a device to discourage smoking. The sensor can basically be designed using methods known in the various arts to detect changes in any measurable physical, chemical, or electrical property: pressure, temperature, positional, air flow or volume (e.g., respiratory changes), electrical impulses, sound, resistance, or frequency. The response of the sensor is then communicated mechanically, optically, or electrically to the stimulus unit.

The invention can be used for animals as well as humans. For example, collars can be fitted for cats and dogs to serve as training aids. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention is a biofeedback device using small jets or streams of a fluid, such as a compressed gas, to tactilely stimulate a selected region of a subject's body. Upon sensing the gas jets, the subject can modify his body position or behavior. The gas jets may produce a positive sensation, providing positive feedback, or may act as an irritant and provide feedback for negative behavior.

Figure 1:
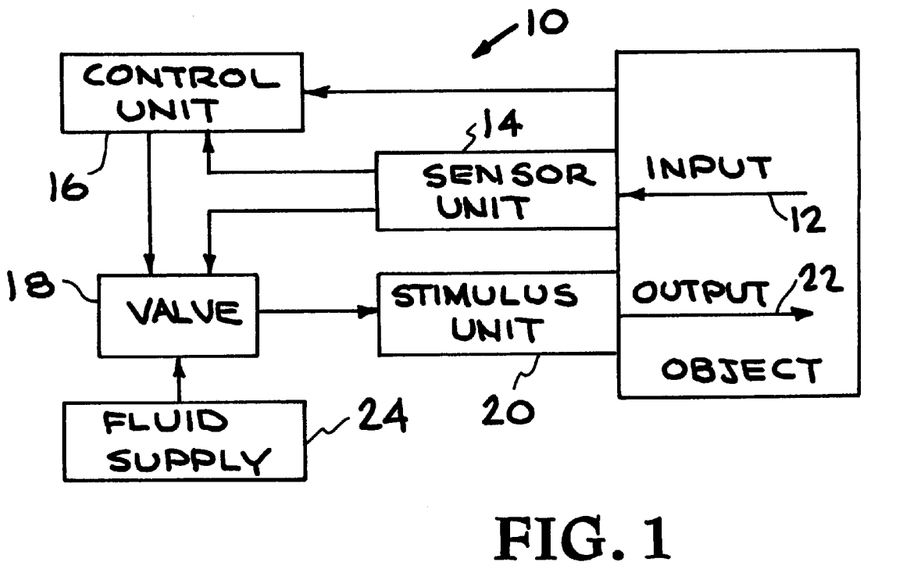
FIG. 1 is a block diagram of a fluid biofeedback device according to the present invention.

FIG. 1 shows a block diagram 10 of the present invention. Input 12 from the subject is detected by a sensor unit 14, which may send a signal (e.g., electrical, optical, radio frequency) to a control unit 16. The control unit 16 may be connected to power unit, such as a battery. The control unit 16 sends a signal to open one or more release valves 18 connected to the stimulus unit 20, which delivers an output 22, specifically one or more bursts of high velocity jets of fluid to a targeted area of the subject. A fluid supply 24 is connected to the stimulus unit 20 via a valve 18 as shown, or it may be incorporated into the stimulus unit 20. Multiple fluid supplies could be used.

Alternatively, the sensor unit 14 may be connected mechanically to directly activate the valve 18 and stimulus unit 20 to produce the jets of fluid, without use of a control unit 16. The fluid supply 24 may be small cylinder or cartridge of liquid water or pressurized/compressed gas such as air or $CO_2$. Other compounds that enhance tactile sensation (e.g., menthol, peppermint, capsacin, palm compounds) could be mixed with the fluid supply 24.

The sensor unit 14 may be connected to the stimulus unit 20 or remote from it, i.e., the sensor may be on another targeted area of the body, or away from the body. The sensor unit 14 and stimulus unit 20 may also have associated power units (e.g., battery) or be activated mechanically. In another embodiment, the stimulus unit 20 may be activated only by the control unit 16, without use of a sensor unit 14. In this case, the control unit 16 may be programmed to activate the release valve 18 and stimulus unit 20 at pre-set intervals (including random intervals) to stimulate the subject.

Figure 2:
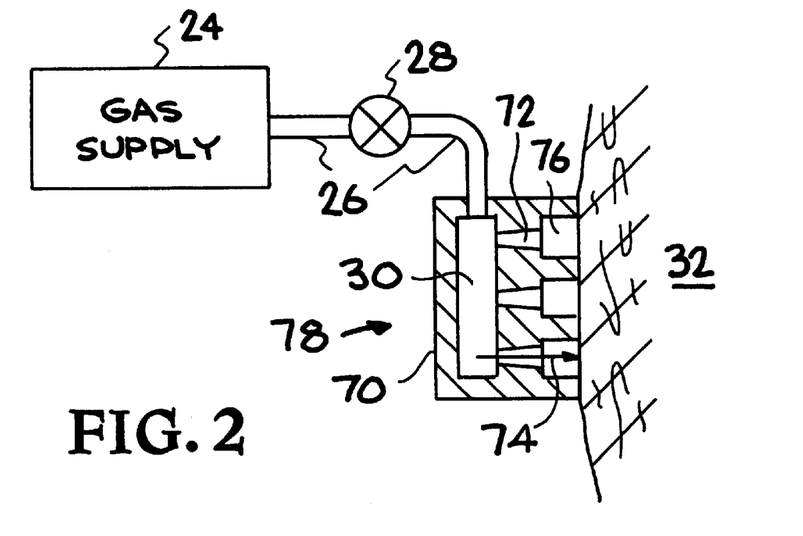
FIG. 2 shows a stimulus unit and gas supply according to the present invention.

FIG. 2 shows an embodiment of a stimulus unit 78 with a gas supply 24 according to the present invention. The unit 78 comprises a housing 70 with a plurality of nozzles 72 having openings 76 leading to the targeted area 32 to be stimulated. The gas supply 24 may be connected to the nozzles 72 through a gas line 26 and manifold chamber 30. The release valve 28, when opened, permits gas from the gas supply 24 to enter the manifold 30 and be ejected (shown by arrow 74) at high velocity through the nozzle openings 76 to cause tactile stimulation.

Figure 3:
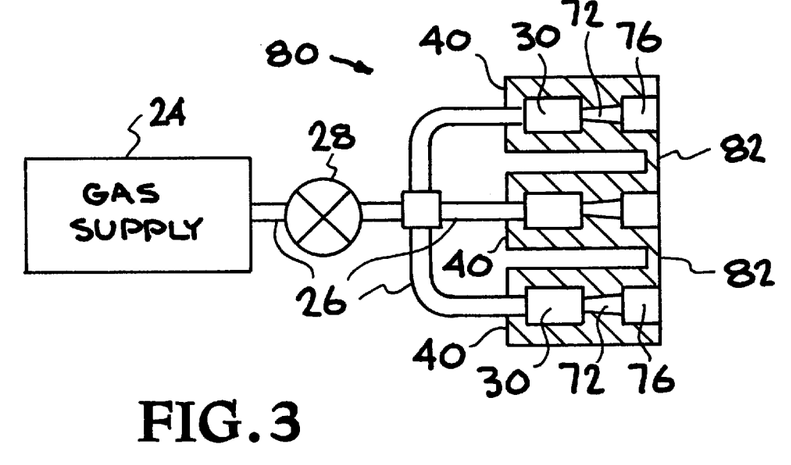
FIG. 3 shows an alternative embodiment of the stimulus unit with flexible modules.
Figure 4:
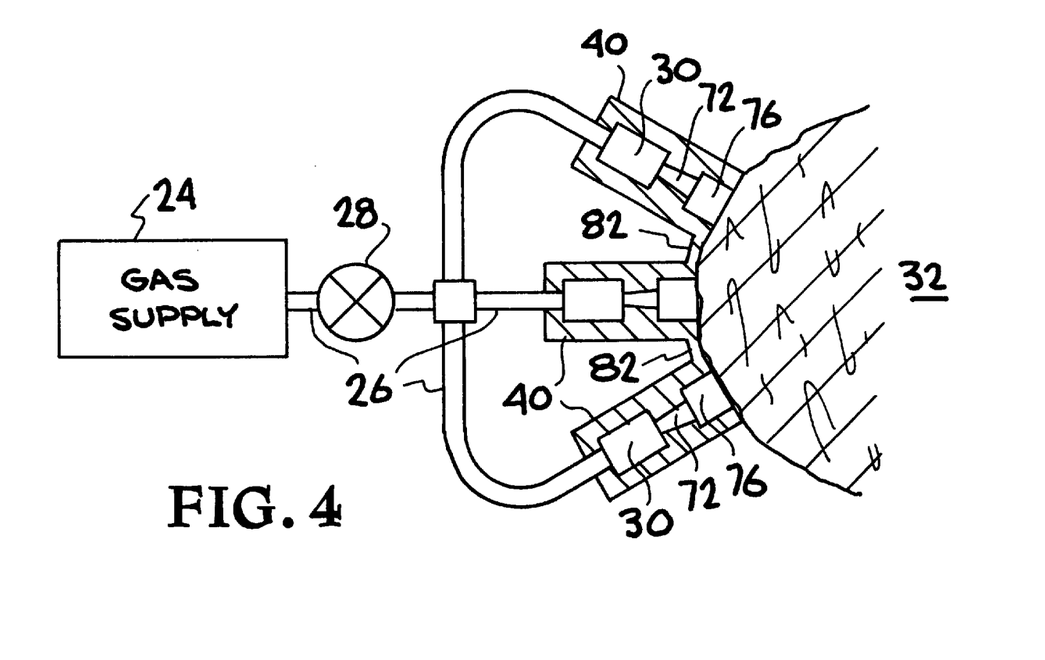
FIG. 4 shows an alternative embodiment of the stimulus unit with flexible modules around a highly contoured surface.

FIG. 3 shows a stimulus unit 80 connected to a gas supply 24 wherein individual nozzles 72 (as shown) or a group of nozzles form stimulator modules 40 that are connected to the gas lines 26 leading to the release valve 28. The modules 40 may be separate housings or they may be connected by a thin flexible section 82 of housing. The thin section 82 allows the modules to be linked yet conform to a shaped surface. Modules abutting a highly contoured surface 32 are shown in FIG. 4. The gas lines 26 also must be flexible enough and of a length to permit the modules 40 to assume the necessary shape. Although FIGS. 3–4 show a linear array of modules, clearly a two-dimensional array or other pattern of modules can be made flexible in two directions to conform to compound curves.

The housing for the stimulus unit may be produced in various sizes and shapes, depending on the area to be targeted. The shapes may include planar, curved, or flat configurations, or a cylindrical form. The gas (or fluid) jets or nozzles (and associated fluid lines) can be made of lightweight plastic, silicon, or foam and may be integrally molded into the stimulus unit housing. The choice of materials and method of manufacture can provide porosity or "breathability" to the stimulus unit. The tips of the nozzles may be tapered or reduced in diameter at various points to allow greater velocities of gas to be generated, thus increasing superficial nerve stimulation with smaller amounts of gas. The nozzle conformation may also alter the amount of audible sound generated by the escaping gas. The sounds can be silenced using muffling materials or baffles, or fringing of final gas escape area.

Figure 5:
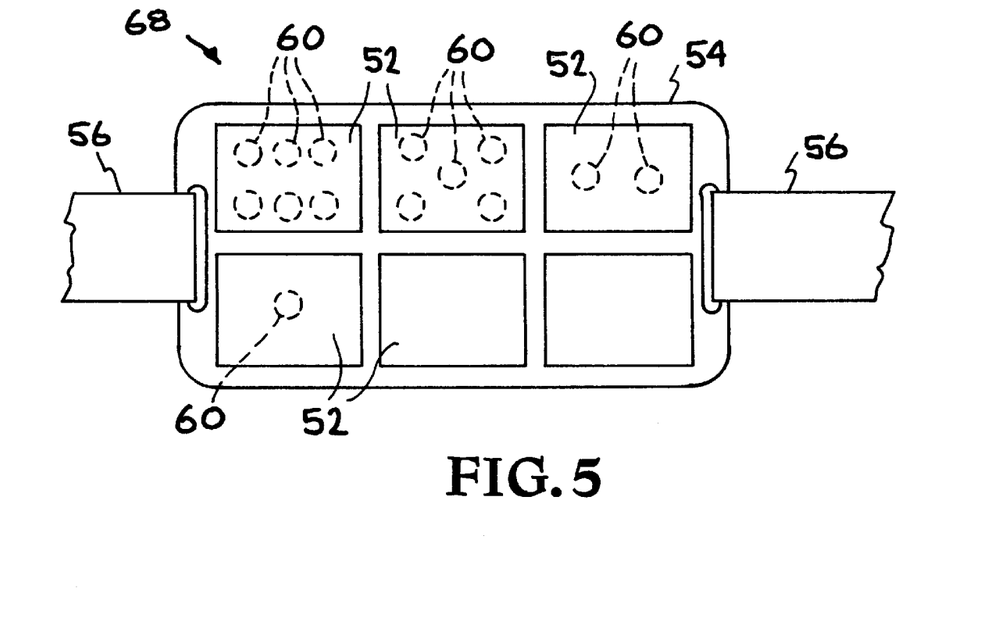
FIG. 5 shows an outer view of a stimulus unit attachable to a belt.

FIG. 5 shows an array of modules 52 generally indicated at 68. The modules 52 are mounted on a flexible substrate 54 that can conform to different places on a body. For example, an adjustable strap 56 can be looped through the substrate 54 to secure the array 68 in the desired location. The modules 52 can have different patterns and numbers of nozzles 60; four such possible patterns are shown with the nozzles in dotted lines. The quantity and pattern of the nozzles 60 is variable.

Figure 6:
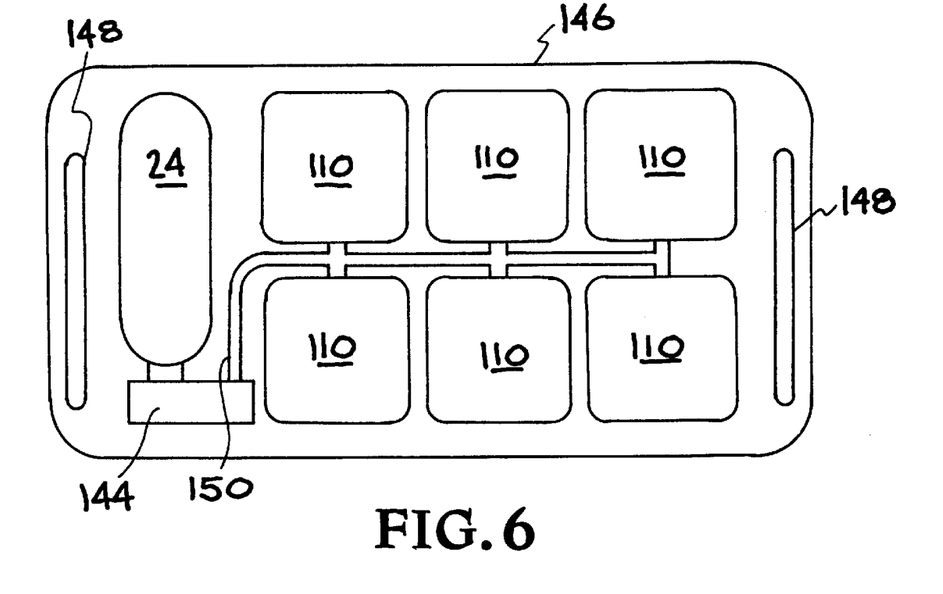
FIG. 6 shows a stimulus unit and gas supply mounted on a flexible pad.

FIG. 6 shows a stimulus unit with six modules 110 mounted on a flexible pad 146. The pad 146 comprises means to maintain the pad in contact with or adjacent to the body. For example, the pad 146 may have loops 148 through which a belt or strap or collar may be threaded. The gas supply 24 is in the form of a replaceable cartridge that connects to a manifold 144. The manifold 144 is connected to a gas line 150, which branches to the individual modules 110.

Figures 7, 8:
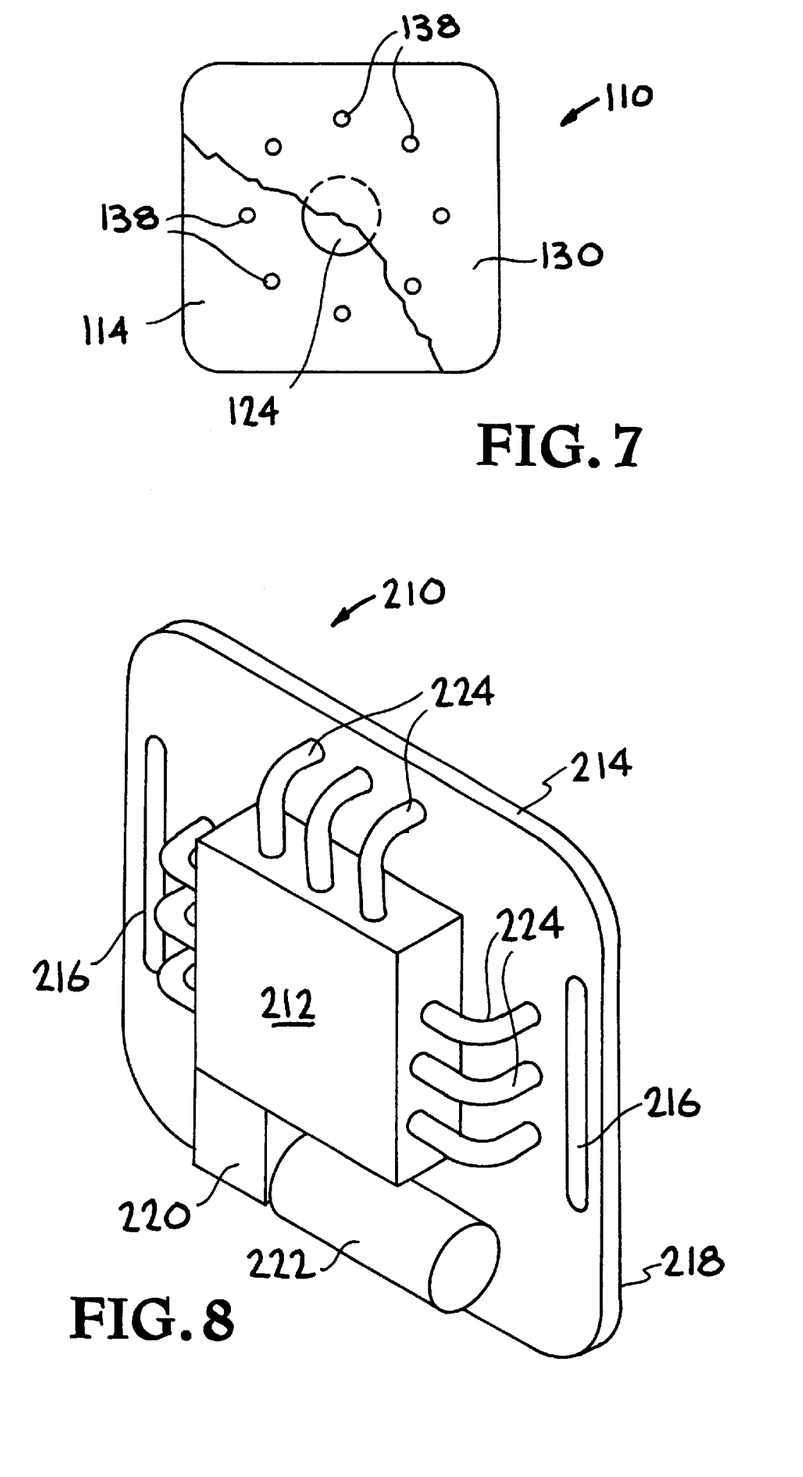
FIG. 7 shows a front view of a stimulator module.
FIG. 8 shows a three dimensional outer view of a stimulator module.

FIG. 7 shows a view of the module 110 facing the body. In this embodiment, a sensor unit 124 is shown in the center of the module 110, surrounded by a circle of nozzles 138. The module 110 may include a flexible membrane or cover on the side facing the body, with openings in the cover aligned with the nozzle openings. The cover is protective and spaced apart from the nozzle tips to avoid contact between the body (or clothing) and the nozzles for safety and hygienic purposes. The nozzles may be spaced apart from the cover by springs. When the sensor unit 124 is activated, such as by pressure exerted by expansion of the abdomen due to relaxation of the abdominal muscles, a release valve between the gas supply and the nozzles 138 is opened, whereby jets of gas shoot at the body, causing tactile sensation.

The sensor unit is designed to be activated, for example, when the abdominal muscles are distended beyond a predetermined limit. When the pressure to the sensor unit is relieved, such as by contracting muscles or altering posture, then the activation or flow of gas jets ceases. The streams of fluid from the nozzles have sufficient velocity to produce a zone of tactile sensation without breaking the skin. Different devices can be designed that have nozzles with different gas exit velocities (e.g., soft vs. hard) to produce the type of sensation desired—pleasant or irritating or startling.

FIG. 8 shows a three dimensional outer view of a stimulator module 210. The module contains a manifold block 212 secured to a flexible mounting pad 214. The pad 214 may include openings 216 through which an adjustable belt or strap can be threaded. Alternatively, the pad may include some other means (e.g., buckles, clips, pins, hooks, snaps, buttons, ties, or fastening tape like Velcro™) for fastening or securing the pad to the body or clothing (permanently or temporarily). The stimulus unit or the entire biofeedback device may be incorporated into a special training garment, or in the case of animals, into a special collar or lead. The manifold 212 faces away from the body and may include a fitting 220 that permits the gas supply 222, such as a gas, fluid, or solid stimulant cartridge, to be easily installed and removed. The manifold 212 has a plurality of small flexible fluid lines 224 leading to the nozzles or jets.

Figure 9:
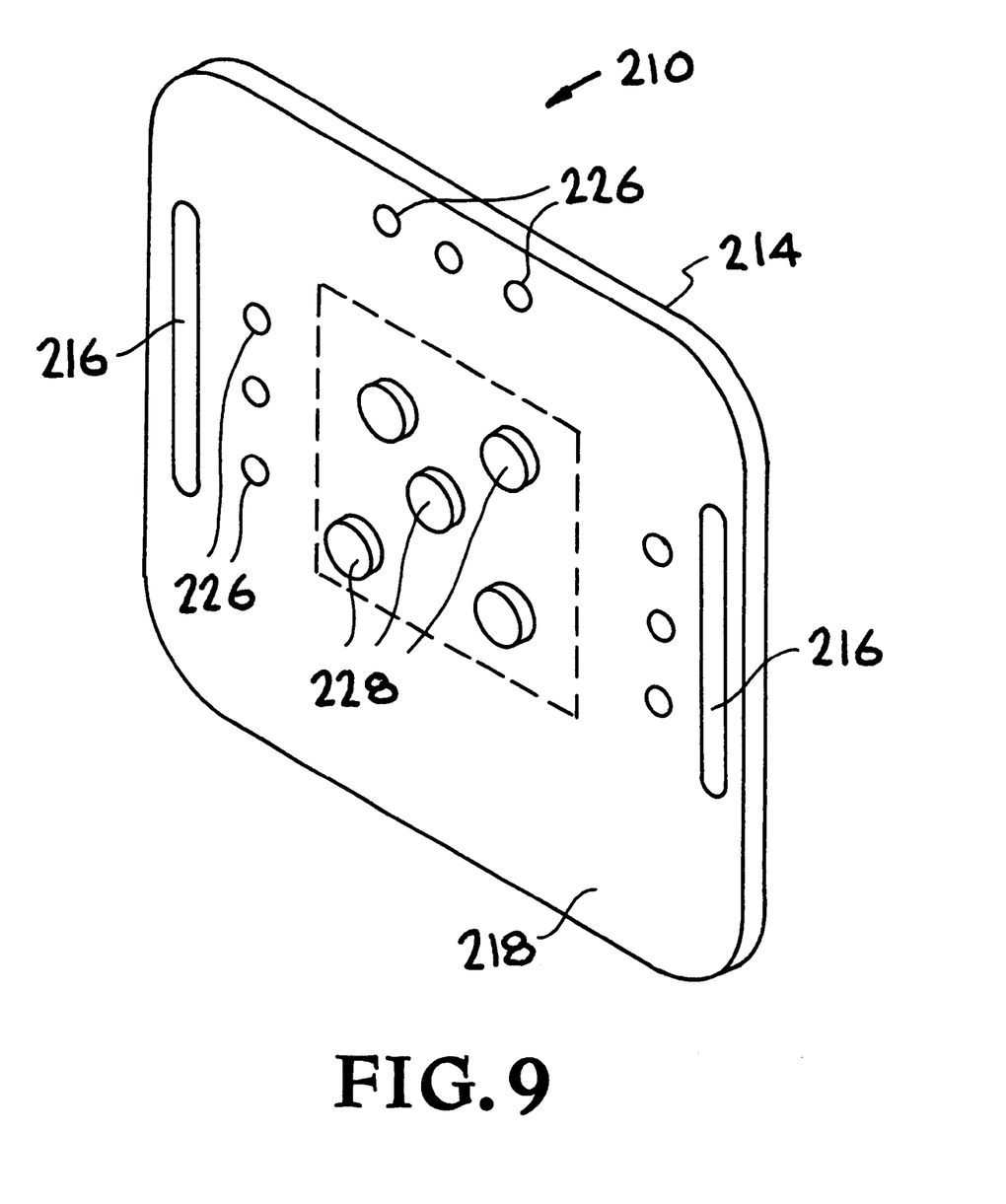
FIG. 9 shows a three dimensional inner view of a stimulator module.

FIG. 9 shows the inner view of the stimulator module 210 of FIG. 8, that is, the side facing the body. The nozzle openings 226 correspond to the fluid lines 224 from the outer side of the module. In this embodiment, the sensor unit is incorporated into the module 210, in the form of one or more sensor release buttons 228. When the force against the buttons 228 exceeds a pre-determined value, the sensor unit causes the fluid release valves connected to the gas supply to open, thereby releasing a burst of gas jets through the nozzle openings 226.

The opening of the fluid release valves may be accomplished mechanically or by an electrical switch. The buttons may be depressed, for example, by the forces secondary to the relaxing abdominal muscles. If a single pressure sensor button 228 is used, then the nozzles may all fire simultaneously. This design may not be optimal, particularly in the event of a defective button. A plurality of sensor buttons 228 as shown may be used, where different buttons are connected to certain nozzles or modules so different sets of nozzles fire independently.

Figure 10:
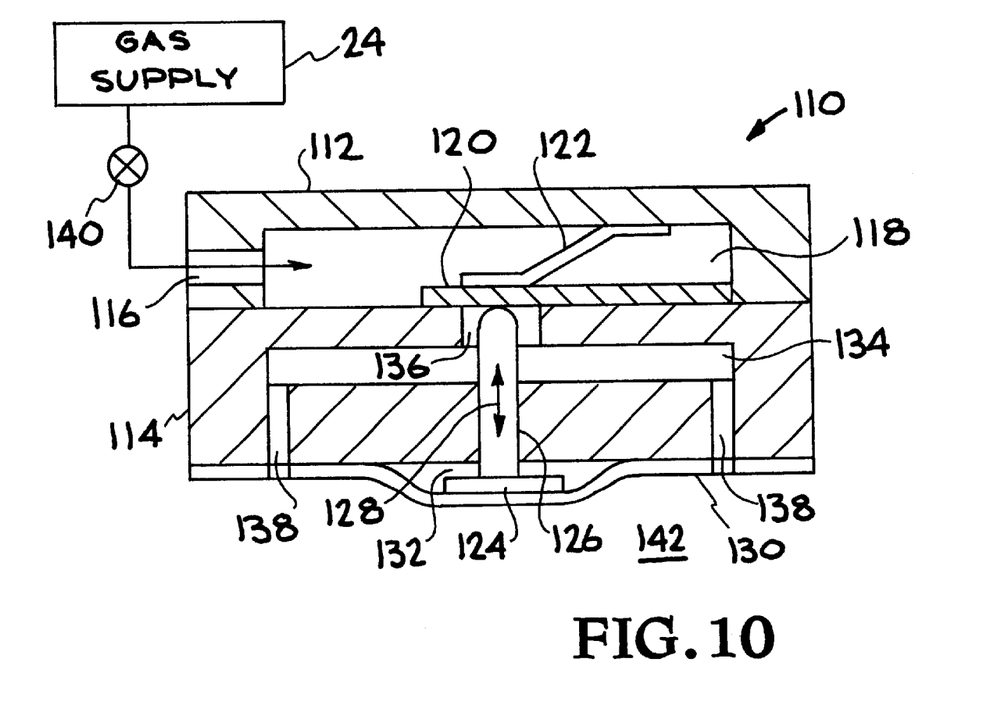
FIG. 10 shows an alternative embodiment of a stimulator module having a closed flapper valve.

FIG. 10 shows an alternative embodiment of a stimulus unit module 110 with gas supply 24. The module 110 has an upper housing 112 and a lower housing 114, which are clamped or bonded together. The upper housing has a gas entry port 116 that allows gas to flow into a fluid chamber 118. The gas is contained in the chamber 118 by a flapper valve 120, which is held in the closed position by a spring 122, such as a leaf spring as shown.

The lower housing 114 incorporates a sensor unit comprising a pressure release button 126 extending through the lower housing to the flapper valve 120, with a head 124 situated on the subject side 142 of the module 110, i.e., facing the subject. The button head 124 is located in a space 132 between the lower housing 114 and a flexible membrane 130, which permits the button 126 to move in one direction shown by arrow 128. The release button 126 in FIG. 10 is shown in the "off" position, being held in place by the spring 122 against the valve 120.

Figure 11:
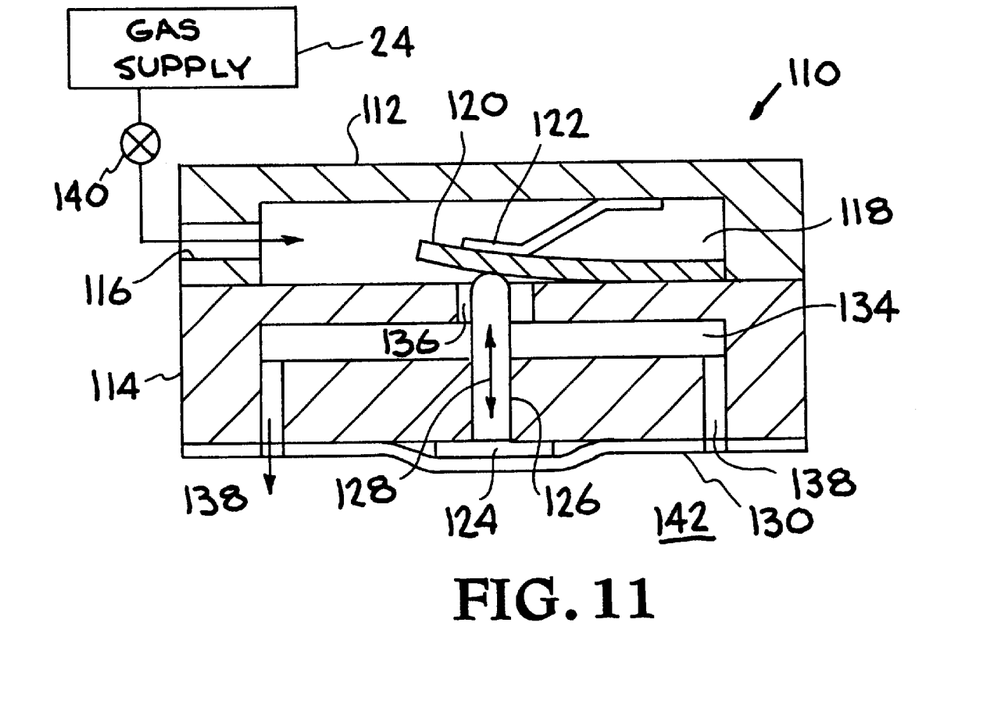
FIG. 11 shows the module of FIG. 10 with an open valve.

When the button 126 is activated (depressed) by pressure from the subject, then the flapper valve 120 is pushed up against the spring 122 into the "on" position, as shown in FIG. 11. Gas in the upper housing 112 gas chamber 118 can escape through port 136 to a chamber 134 in the lower housing 114, and then be ejected through nozzles 138 to the subject side 142. When the pressure against the button head 124 is relieved, the spring 122 will close off the flapper valve 120, and the flow of gas through the nozzles 138 ceases. A release valve 140 between the gas supply 24 and the chamber 118 can permit gas to flow into the chamber 118 at any time or only when the flapper valve 120 is opened. The valve 140 may be activated by a control unit when the sensor unit is activated.

The module 110 can be designed with any number of sensor units (e.g., pressure buttons) and nozzles. The design of two nozzles per sensor unit as shown in FIGS. 10–11 is illustrative only, and the skilled artisan will readily appreciate that the number of sensor buttons and nozzle openings can be varied.

Although the sensor units shown in FIGS. 7, 9–11 illustrate pressure sensor units for biofeedback devices involving abdominal and back muscles, the sensor unit is designed for the particular behavior or body condition to be targeted by the subject, including the generation of a selected chemical analyte. The sensitivity of the sensor may be set electronically or mechanically. In addition, the opening of the fluid release valve(s) in response to the sensor unit may be accomplished mechanically or by an electrical switch.

A sensor unit may comprise a sensor that is incorporated into or mechanically connected to an electronic circuit element (e.g., capacitor, inductor, resistor) in an electronic circuit in the control unit to cause a change in the electrical characteristics of the circuit in a measurable way in response to changes in the sensor. For example, changes induced in the value of a capacitor or inductor when the sensor changes physical properties (e.g., volume, position) or electrical or electrochemical properties alter the resonant frequency of an L-C resonator circuit. Similarly, varying the value of a resistor leads to a measurable change in the R-C time constant of a discharging capacitor circuit.

Changes in the electrical characteristics of the circuit can be detected remotely by the stimulus unit using an electronic interrogation device. Examples of interrogation methods include (1) frequency dependent electromagnetic loading of an interrogator antenna by a passive resonator sensor circuit, and (2) audio monitoring of a tone chirped by the voltage of discharging R-C circuit. The control unit can powered by the interrogator device in the stimulus unit, or the control unit circuit element may be designed for passive interrogation.

Figure 12:
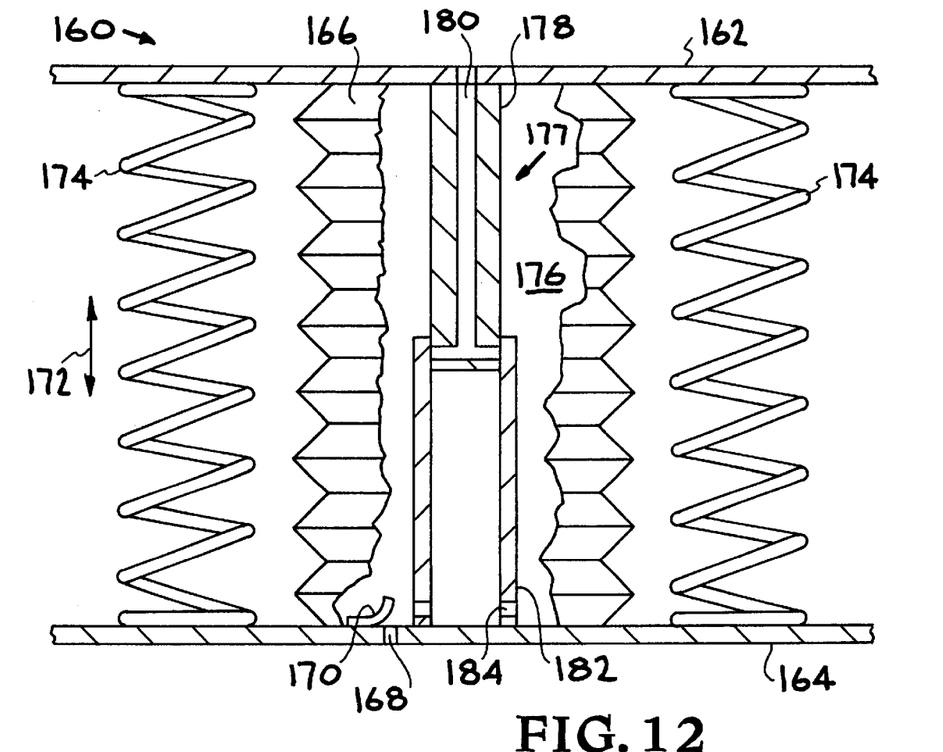
FIG. 12 shows an embodiment of a self-powered stimulation module using bellows and springs.

Another embodiment of the invention for abdominal and posture training is shown in FIG. 12. A self-powered air stimulator module is generally indicated at 160, where one side 162 of the module 160 is adjacent the body. A cylindrical bellows structure 166 is situated between and fastened to the two sides 162,164 of the module 160. A port 168 on side 164 leads to the internal volume 176 of the bellows 166. The port 168 is closed by a flapper valve 170. Springs 174 on either side of the bellows 166 have a low spring rate and provide just enough force to move the two sides 162,164 apart from each other as indicated by arrow 172. This movement of the springs 174 and bellows 166 creates a vacuum internal to the bellows, and atmospheric pressure will push open the flapper valve 170, admitting air into the internal volume 176 of the bellows 166.

A sliding valve structure 177 may be located in the internal volume 176 of the bellows 166. This structure 177 has a piston 178 mounted on side 162 and having a T-shaped port 180 corresponding to an opening in side 162. The piston 178 is free to slide within cylinder 182, which is mounted on side 164 and provides a guide for the module 160.

Figure 13:
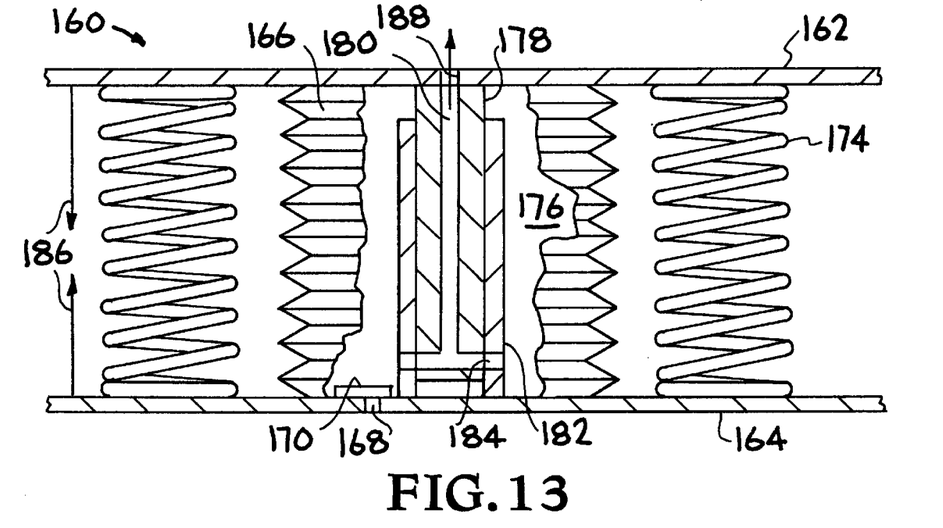
FIG. 13 shows the embodiment in FIG. 12 in a compressed position.

In FIG. 13, the two sides 162,164 have been compressed as indicated by arrows 186. Air is compressed in the volume 176 within the bellows 166. Before the piston 178 hits side 164, the piston port 180 and a port 184 in cylinder 182 will line up, allowing the compressed air in the bellows 166 to flow through the ports 180,184. The air flows from the internal volume 176 through ports 180,184 and out of opening 188 on side 162 to stimulate the subject. When the subject reacts by contracting muscles, the springs 174 will push the sides 162,164 apart, filling the bellows 166 once again with air.

Figure 14:
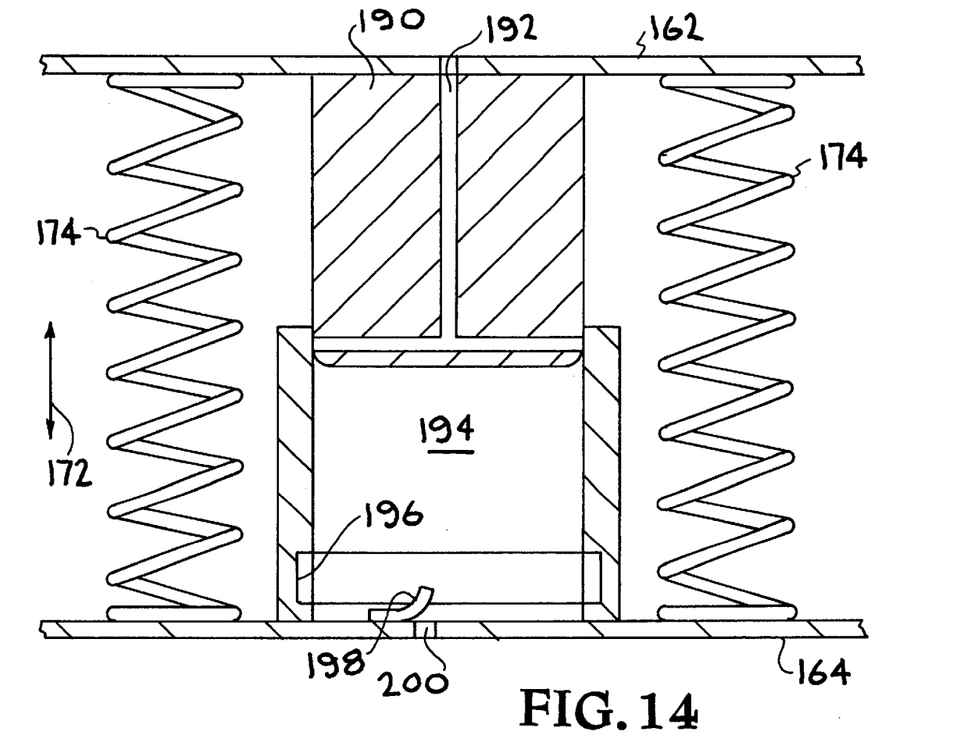
FIG. 14 shows an alternative embodiment of a self-powered stimulation module using a piston and cylinder mechanism.
Figure 15:
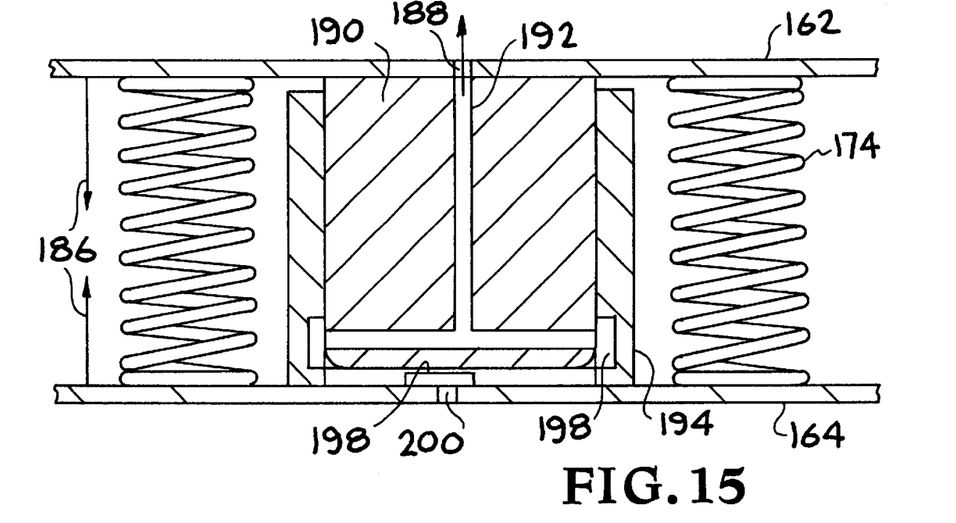
FIG. 15 shows the embodiment in FIG. 14 in a compressed position.

FIGS. 14–15 show an alternative embodiment of the device, where the bellows has been replaced by a piston 190 and cylinder 194 mechanism. The piston 190 is fixed to side 162 and has a port 192 corresponding to an opening in side 162. The piston 190 is free to slide within the cylinder 194, which has an annular shaped port 196. As the sides 162,164 are pushed away from each other by springs 174 as indicated by arrow 172, air is drawn into the cylinder 194 through port 200 and flapper valve 198.

In FIG. 15, the sides 162,164 have been compressed as indicated by arrows186. Air is compressed in the cylinder 194 as the piston 190 slides down the cylinder 194. When the ports 192,196 line up, air flow can occur out of the module through a small opening188. This flow of air to the subject provides stimulation. Although a single opening has been shown in the embodiments in FIGS. 12–15 to illustrate the basic functioning of the module, it is readily apparent to those skilled in the art that the module can be designed with a plurality of openings for each piston or bellows.

The above descriptions and illustrations are only by way of example and are not to be taken as limiting the invention in any manner. It is obvious that one skilled in the art can substitute known equivalents for the structures and means described. The full scope and definition of the invention, therefore, is set forth in the following claims.

What is claimed is:

1. A biofeedback apparatus, comprising:
    a stimulus unit comprising means for controllably ejecting jets of a fluid at a selected portion of a body, wherein the stimulus unit can be secured adjacent the body;
    a fluid supply connected to the stimulus unit through a fluid line and a release valve; and
    means to activate the release valve, whereby jets of fluid are ejected at the body, in response to a selected behavior of the body, to produce a tactile sensation to alert the user to modify body position or behavior.

2. The apparatus as recited in claim 1, wherein mechanical means activate the release valve.

3. The apparatus as recited in claim 1, wherein electrical means activate the release valve.

4. The apparatus as recited in claim 1, further comprising a sensor unit which comprises the means to activate the release valve.

5. The apparatus as recited in claim 4, wherein the sensor unit is connected to the stimulus unit.

6. The apparatus as recited in claim 4, wherein the sensor unit is remote from the stimulus unit.

7. The apparatus as recited in claim 4, wherein an electrical signal from the sensor unit activates the release valve.

8. The apparatus as recited in claim 4, wherein a radiofrequency signal from the sensor unit activates the release valve.

9. The apparatus as recited in claim 4, wherein the sensor unit comprises a pressure sensor for detecting pressure exerted by a selected portion of the body.

10. The apparatus as recited in claim 4, wherein the sensor unit comprises a position sensor.

11. The apparatus as recited in claim 4, wherein the sensor unit comprises a vibration senasor.

12. The apparatus as recited in claim 4, wherein the sensor unit comprises a temperature sensor.

13. The apparatus as recited in claim 4, wherein the sensor unit comprises a sensor that detects sound patterns.

14. The apparatus as recited in claim 4, wherein the sensor unit comprises a chemical sensor for detecting a chemical analyte emitted by the body.

15. The apparatus as recited in claim 4, wherein the sensor unit comprises a sensor for detecting an electrical signal produced by the body.

16. The apparatus as recited in claim 1, further comprising a control unit which comprises the means to activate the release valve.

17. The apparatus as recited in claim 16, wherein an electrical signal from the control unit activates the release valve.

18. The apparatus as recited in claim 1, wherein the stimulus unit comprises a plurality of nozzles through which the jets of fluid are ejected.

19. The apparatus as recited in claim 18, wherein the stimulus unit further comprises a flapper valve through which the fluid flows to the nozzles when the flapper valve is open.

20. The apparatus as recited in claim 18, further comprising a control unit comprising the means to activate the release valve; and a sensor unit comprising a sensor; wherein the control unit is activated to open the release valve when the sensor is activated.

21. The apparatus as recited in claim 20, wherein the control unit further comprises an electronic circuit element that is operably connected to the sensor.

22. The apparatus as recited in claim 18, further comprising a control unit comprising the means to activate a plurality of release valves; and a sensor unit comprising a sensor; wherein the control unit is activated to selectively open at least one release valve when the sensor is activated.

23. The apparatus as recited in claim 1, wherein the fluid comprises a gas.

24. The apparatus as recited in claim 1, wherein the fluid supply comprises a compressed gas.

25. The apparatus as recited in claim 1, wherein the fluid comprises a substance to enhance tactile sensation.

26. A biofeedback apparatus, comprising:

a stimulus unit housing, wherein the unit can be secured adjacent a body;

a chamber in the housing having a volume that can contain air;

means for compressing and expanding the volume of the chamber; and means for controllably ejecting air at a selected portion of the body, in response to a selected behavior of the body, to produce a tactile sensation to alert the user to modify body position or behavior, wherein said air is controllably ejected through outlet ports in the housing when the volume in the chamber is compressed.

27. The apparatus as recited in claim 26, wherein the means for compressing and expanding comprise a bellows and a spring.

28. The apparatus as recited in claim 26, wherein the means for compressing and expanding comprise a piston and a spring.

29. A biofeedback method, comprising:

controllably ejecting jets of a fluid at a selected portion of a body in response to a selected behavior of the body to produce a tactile sensation to alert the user to modify body position or behavior.

* * * * *